United States Patent [19]

Cecco et al.

[11] Patent Number: 5,117,182

[45] Date of Patent: * May 26, 1992

[54] FERROMAGNETIC EDDY CURRENT PROBE HAVING MULTIPLE LEVELS OF MAGNETIZATION

[75] Inventors: Valentino S. Cecco; Jon R. Carter, both of Ontario, Canada

[73] Assignee: Atomic Energy of Canada Limited, Ottawa, Canada

[*] Notice: The portion of the term of this patent subsequent to Aug. 8, 2006 has been disclaimed.

[21] Appl. No.: 535,521

[22] Filed: Jun. 8, 1990

[51] Int. Cl.⁵ .................... G01N 27/90; G01R 33/12
[52] U.S. Cl. ................... 324/220; 324/225; 324/232; 324/242
[58] Field of Search ............... 324/219-221, 324/233-243, 260-262

[56] References Cited

U.S. PATENT DOCUMENTS

| | | | |
|---|---|---|---|
| 4,107,605 | 8/1978 | Hudgell | 324/220 |
| 4,468,619 | 8/1984 | Reeves | 324/220 |
| 4,704,577 | 11/1987 | Junker et al. | 324/220 |
| 4,808,924 | 2/1989 | Cecco et al. | 324/220 |
| 4,808,927 | 2/1989 | Cecco et al. | 324/220 |
| 4,855,676 | 8/1989 | Cecco et al. | 324/220 |

Primary Examiner—Kenneth A. Wieder
Assistant Examiner—Warren S. Edmonds
Attorney, Agent, or Firm—Gowling, Strathy & Henderson

[57] ABSTRACT

Eddy current probes for detecting defects in a ferromagnetic tube are disclosed. The probe uses partial magnetic saturation and includes two or more eddy current measuring coil assemblies in a probe housing. The coil assemblies are spaced apart from each other and located at positions of different magnetic saturation.

19 Claims, 3 Drawing Sheets

FERROMAGNETIC EDDY CURRENT PROBE HAVING MULTIPLE LEVELS OF MAGNETIZATION

FIELD OF THE INVENTION

This invention relates to an eddy current probe for detecting localized defects in a tube made of a ferromagnetic material. More specifically, the invention relates to a ferromagnetic tube inspection technique which utilizes an eddy current probe operating in two or more partial magnetic saturation levels.

BACKGROUND OF THE INVENTION

In the past, bodies of ferromagnetic material have been inspected by a method such as the flux leakage method as taught, for example, in U.S. Pat. No. 3,091,733 (May 28, 1963, Fearer et al), 4,468,619 Aug. 28, 1984, Reeves), and 4,602,212 (Jul. 22, 1986, Hiroshima et al). In this method, the metal is magnetized in a direction parallel to its surface. At defects or where regions of the metal body are not uniform, some magnetic flux passes into the air and may be detected by sensors located nearby, thus giving an indication of the presence of faults, non-uniformity, etc.

U.S. Pat. No. 4,107,605 (Aug. 15, 1978, Hudgell) discloses an eddy current technique for detecing abnormalities in a pipeline of a ferromagnetic material. The eddy current probe includes a plurality of spiral sensing coils placed with their axes normal to the surface of the pipeline wall and connected on four legs of an AC bridge, thus compensating for lift-off. A biasing magnetic field by a permanent magnet permits distinguishing internal from external defects in weakly ferromagnetic tubes by comparing outputs from systems with and without biasing field. A partial magnetic saturation is achieved but the sensing coils are placed at one location with a saturation level. No multiple saturation levels are employed.

U.S. Pat. Nos. 3,952,315 (Apr. 20, 1976, Cecco) and 2,964,699 (Dec. 6, 1960, Perriam) describe eddy current probes for use of testing weakly ferromagnetic tubes. They both include magnetic saturation means. Their eddy current sensing coil assembly is located at a place with one magnetic saturation level.

In U.S. Pat. Nos. 2,992,390 (Jul. 11, 1961, de Witte) and 3,940,689 (Feb. 24, 1976, Johnson, Jr.) special electromagnetic ways of generating magnetic fields are taught in connection with the eddy current testing in that de Witte uses uniquely designed cores for transmit-receive coils and Johnson, Jr. employs a solenoid wound about a core of a substantial length. There are no teachings about two or more levels of magnetization.

OBJECTS OF THE INVENTION

It is therefore an object of the present invention to provide an eddy current probe for inspecting ferromagnetic tubes which is sensitive to defects but relatively immune to noises such as those from magnetite deposits and permeability variations.

It is still another object of the present invention to provide an eddy current probe for inspecting ferromagnetic tubes which includes magnetization means and at least two eddy current sensing means for both good sensitivity to defects but relatively immune to noises.

It is a further object of the present invention to provide an eddy current probe for inspecting ferromagnetic tubes which includes at least two eddy current sensing means located at different magnetic saturation levels.

SUMMARY OF THE INVENTION

Briefly stated, in accordance with the present invention, an eddy current probe for detecting defects in a tube made of a ferromagnetic material includes a probe housing made of a non-ferromagnetic material. The housing is shaped to be introduced into the tube under inspection and has an axis substantially coinciding with the axis of the tube when the probe is in use. The probe further includes magnetization means for generating magnetic field there about and for magnetizing the tube to partial saturation levels. At least two substantially identical eddy current measuring means are provided in the housing and are spaced apart axially from each other at locations of different saturation levels.

BRIEF DESCRIPTION OF THE DRAWINGS

In a more complete understanding of the present invention and for further objects and advantages thereof, references may be made to the following description taken in conjunction with the accompanying drawings in which.

DETAILED DESCRIPTION OF THE PREFERRED EMBODIMENTS

Conventional eddy current testing detects changes in eddy current induced in an object under test. The eddy current is indirectly measured by a probe coil located near the surface of the object which monitors the magnetic flux created by the eddy current. However, when an eddy current probe is used for ferromagnetic tube inspection, the magnetic permeability of the ferromagnetic material affects the probe coils inductance as well as depth of eddy current penetration into the material. The magnetic permeability strongly depends on factors such as:
thermal processing history;
mechanical processing history;
chemical composition;
internal stresses; and
temperature (if close to Curie temperature).

The large variations in permeability make conventional eddy current testing for defects in magnetic materials very difficult.

The best solution of eddy current testing of a magnetic material for defects is to bring it to a condition where $\mu_r = 1.0$. Relative incremental or recoil permeability, $\mu_r$, is defined as $\mu_r = \Delta B/\Delta H$ where $\Delta B$ is the change in flux density which accompanies a change in magnetizing force, $\Delta H$ created for example by an eddy current coil's alternating current.

A few slightly magnetic materials can be heated above their Curie temperature to make them nonmagnetic. Monel TM 400 heated to between 50° and 70° C. has been tested in this manner. Most materials, however, have too high a Curie temperature to be tested by this approach. The only other way to decrease $\mu_r$ to unity is by magnetic saturation.

Figure 1:
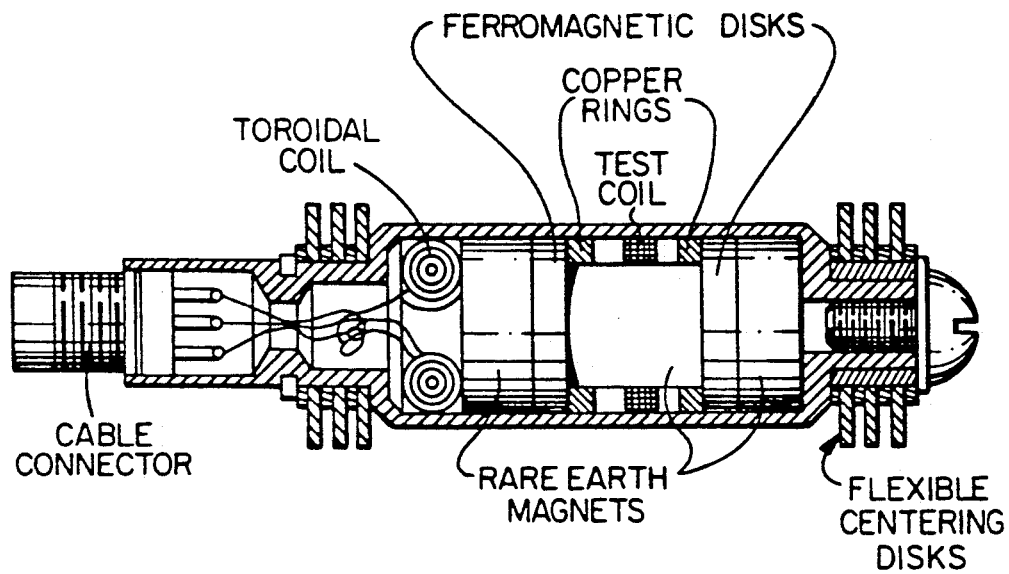
FIG. 1 is a schematic view of a prior art eddy current probe.

FIG. 1 shows a probe known in the art as the saturation probe which incorporates a permanent magnet configuration designed to maximize the saturation field over the test coil.

Figure 2A:
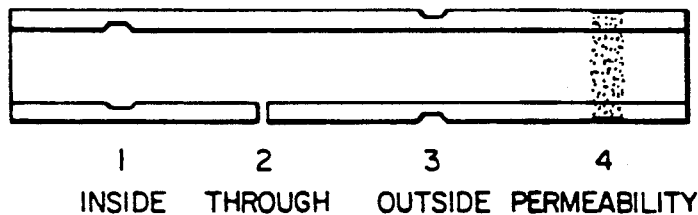
FIGS. 2(a), 2(b) and 2(c) show a ferromagnetic stainless steel test tube and signals obtained by the probe shown in FIG. 1.
Figure 2B:
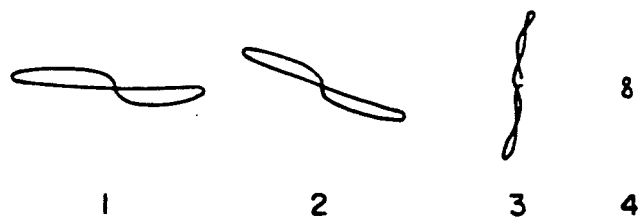
Figure 2C:
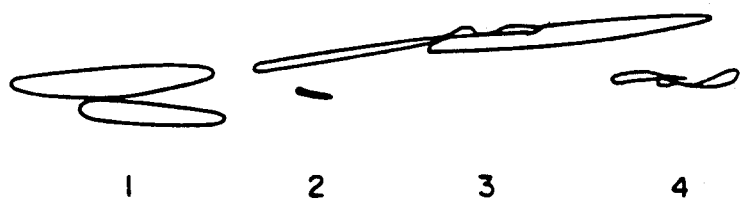

The importance of achieving maximum saturation is illustrated in FIGS. 2(a), 2(b) and 2(c) which show results from Type 439 stainless steel heat exchanger tube. (See NDT International, Vol. 22, No. 4, August 1989, pp. 217-221.) A 15.9 mm OD by 1.2 mm thick tube with internal and external calibration defects and a shot peened area was used to compare the performance of various saturation probes. As shown in FIG. 2(a), the external defects ranged from 20 to 100% deep. FIG. 2(b) shows the signals obtained with a probe capable of 98% saturation and FIG. 2(c) signals with 89% saturation. The relative magnetic permeability ($\mu_r$) at 98% saturation is approximately 1.15 and at 89% saturation it is 1.8. At 98% saturation the eddy current signals from the external calibration holes display the characteristic phase rotation with depth, that one expects for nonmagnetic materials. In contrast, with only 89% saturation the signals are distorted and indistinguishable from "change in magnetic permeability" signals. From similar tests on other ferromagnetic tubes it has been found that at least 98% saturation is needed ($\mu_r \leq 1.2$) for reliable test results. This requires detailed optimization of the saturation magnet design for each ferromagnetic tube material. The magnet configuration shown in FIG. 1 is designed to achieve the strongest saturation possible and is suitable for stainless steel. However, even the strongest saturation probe such as this cannot completely saturate some tubes especially carbon steel tubes or pipes.

Contrary to past belief, it has recently been realized that a partial magnetic saturation is sufficient for detecting defects in carbon steel by eddy current.

Figure 3:
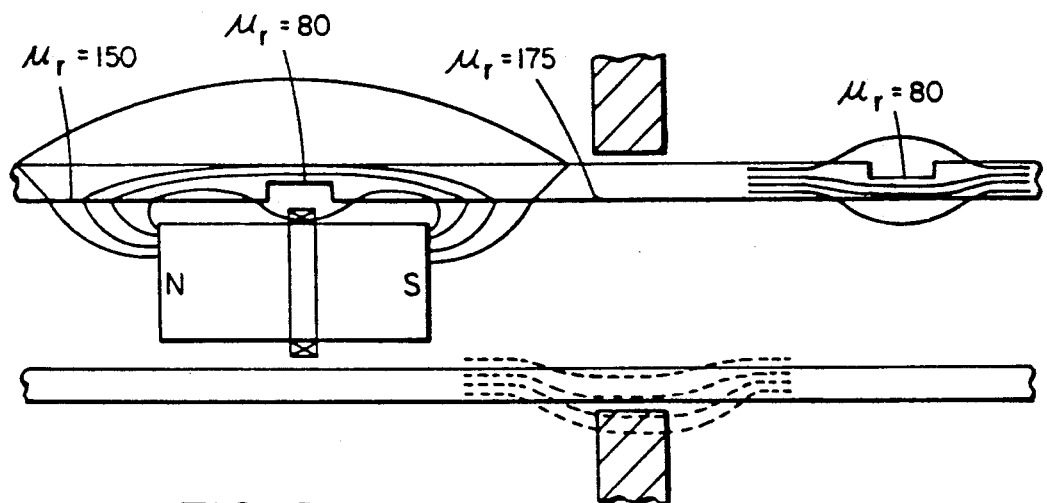
FIG. 3 is a diagrammatic view of a partial saturation probe of a known design being used for a carbon steel testing.

FIG. 3 illustrates diagrammatically the function of such a partial saturation probe. The magnetic field is schematically shown in the case of a carbon steel tube with variations of the wall thickness and the support plate. The figure also indicates relative magnetic permeability ($\mu_r$) at various locations. The probe detects these changes of the relative magnetic permeability.

Also, U.S. Pat. No. 4,855,676 (Aug. 8, 1989, Cecco et al) describes an eddy current probe of the transmit-receive coil type for inspecting a ferromagnetic tube. The probe uses only partial magnetic saturation (e.g. less than 50%) but still achieves sufficient sensitivity to defects in thin and thick tubes of a weak or strong magnetic material.

The present invention improves further the partial saturation eddy current probes for ferromagnetic tubes (e.g. carbon steel tubes). The eddy current sensing means can be of the transmit-receive type as well as the absolute or differential sensing impedance type.

Figure 4:
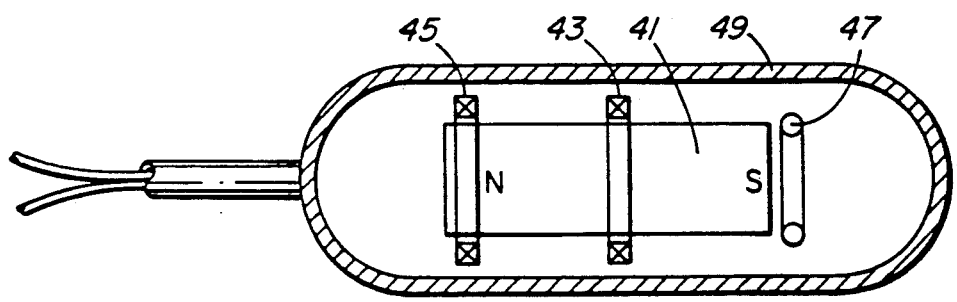
FIG. 4 is a schematic view of an eddy current probe of the present invention according to one embodiment using a bobbin coil configuration.

Referring to FIG. 4, an eddy current probe of the absolute type is shown, according to one of the preferred embodiments of the present invention. In this embodiment, two eddy current measuring assemblies are located spaced apart over a permanent magnet 41. The assemblies include a first bobbin test coil 43 and a second bobbin test coil 45 which are substantially identical in construction to one another. The assemblies further include a common reference coil 47 (e.g. of the toroidal configuration). The test coils 43 and 45, together with the common reference coil 47, produce signals indicative of localized eddy current in a ferromagnetic tube under inspection. The permanent magnet 41 generates a toroidal magnetic field about it past the non-ferromagnetic housing 49 to magnetically saturate the tube to a level desired. As shown in the figure as one of the preferred embodiments, the test coils are located spaced apart where the magnetic field strength, thus the saturation level, is different in that the coil 43 is at the maximum partial saturation level and the coil 45 at a weaker level. Therefore, the coil 43, with the aid of the reference coil 47, has the maximum sensitivity for detecting defects. The location of the coil 45, on the other hand, can be selected to the area where the partial saturation level is optimum for the sensitivity to particular anomalies which are desired to be distinguished from other types. The coil 43 at the maximum partial saturation level will detect a change in $\mu_r$ with a decrease in wall thickness (defect). The coil 45 at a lesser saturation level will not detect a change in $\mu_r$. It is because $\mu_r$ is constant up to a magnetic level called $B_{transition}$. However, both coils will detect a change in tube magnetic permeability, magnetite deposits, tube expansion, etc., which are considered as false defect indications and, therefore, treated as noises. Therefore, if both coils detect an anomaly it is a false indication, if only the coil 43 detects an anomaly it is a defect. In this way, it is possible to separate defect signals from false indications.

For example, in the case of heat exchangers made of carbon steel, the maximum partial saturation level is good for detecting all the defects while a lower saturation level which has been properly selected, is used for detecting all the anomalies which normally are considered as false defect indications.

Also, to detect defects under support plates requires optimum partial magnetization; too high a field results in a large support plate signal, too low results in a small defect signal and large background noise. A probe with 2 or 3 levels of saturation would allow flexibility of picking appropriate levels dependent on test/material conditions.

Figure 5:
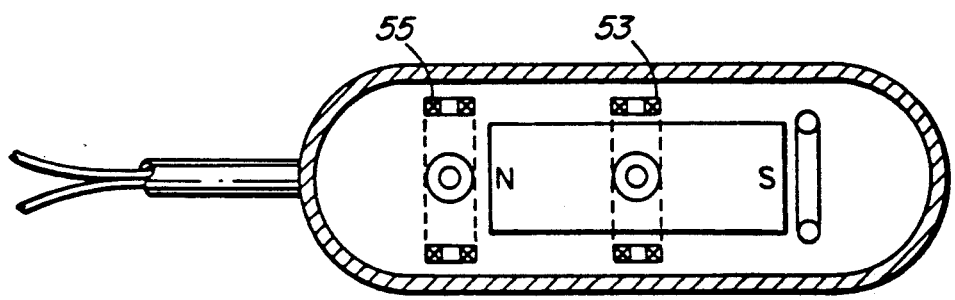
FIG. 5 is a schematic view of an eddy current probe of the present invention according to another embodiment using a pancake coil configuration.

In FIG. 5, two bracelets containing pancake coils 53 and 55 are substituted for the bobbin coils of FIG. 4. This configuration is more suitable for some specialized conditions such as internal defects and cracks.

Figure 6:
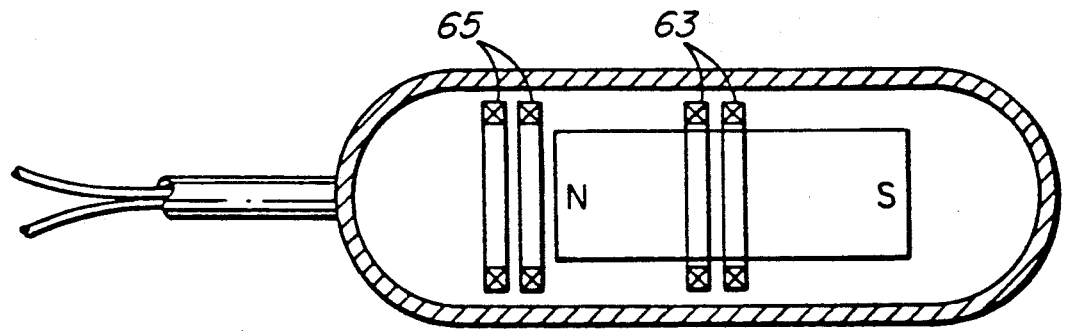
FIG. 6 is a schematic view of an eddy current probe of the present invention according to still another embodiment of a differential coil configuration.

Another embodiment is illustrated in FIG. 6. In this embodiment, a pair of bobbin coils are provided to form each of the eddy current measuring assemblies 63 and 65. The pairs function as the differential probe and located at different partial saturation levels.

Figure 7:
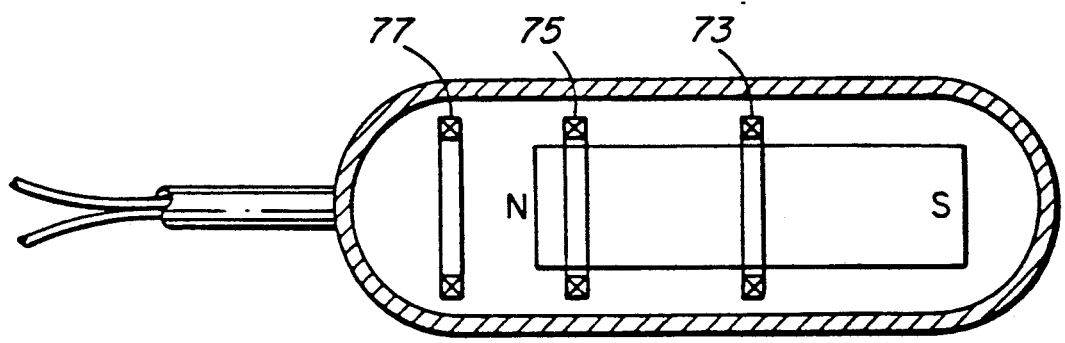
FIG. 7 is a schematic view of an eddy current probe of the present invention according to still another embodiment showing three eddy current measuring coil assemblies.

A further embodiment is shown in FIG. 7 in which three eddy current measuring assemblies 73, 75 and 77 are used at locations of three different saturation levels.

The probe can distinguish more finely various kinds of defects, such as defects under support plates.

Figure 8:
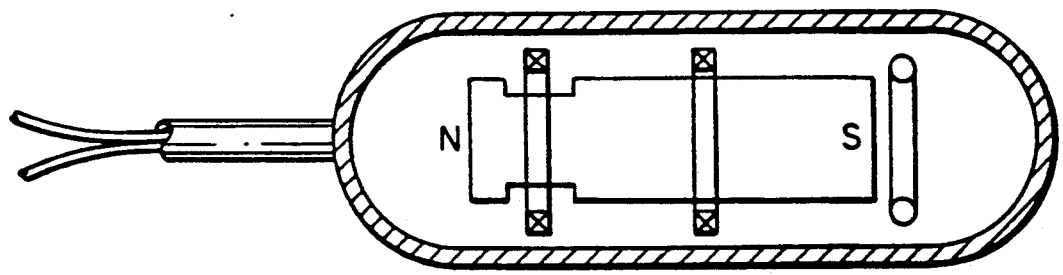
FIG. 8 is a schematic view of an eddy current probe of the present invention according to yet another embodiment showing a specific magnet configuration.

In FIG. 8 there is illustrated still another embodiment of the present invention. In this embodiment one of various ways of creating a specific magnetic field distribution having a greater difference in the magnetization level is shown. A magnet is designed to have a specifically designed shape or to be provided locally with a different material so that a certain location has a weaker magnetic field.

We claim:

1. An eddy current probe for detecting defects in a tube made of a ferro-magnetic material, comprising:
   a probe housing made of a non-ferromagnetic material and shaped to be introduced into the tube for inspection, said housing having an axis substantially coinciding with the axis of the tube under inspection when the probe is in use;
   magnetization means for generating a magnetic field within the probe housing and for magnetizing said tube to partial saturation levels, and
   at least two substantially identical eddy current measuring means in said housing, the said eddy current measuring means being spaced apart axially from each other at locations of different saturation levels.

2. The eddy current probe according to claim 1 wherein:
   one of the said at least two eddy current measuring means is positioned at the maximum partial saturation level; and
   each of the others thereof is positioned at a saturation level different from the said maximum level.

3. The eddy current probe according to claim 2 wherein:
   each of the said current measuring means comprises a pair of identical eddy current measuring coil assemblies, electrically connected to operate in the differential probe configuration.

4. The eddy current probe according to claim 2 wherein:
   the said at least two substantially identical eddy current measuring means comprise at least two substantially identical eddy current measuring coil assemblies located spaced apart axially from each other at locations of different saturation levels and a common reference coil, all electrically connected to operate in the absolute probe configuration.

5. The eddy current probe according to claim 3 wherein:
   the said pair of eddy current measuring coil assemblies are of bobbin type.

6. The eddy current probe according to claim 3 wherein:
   the said pair of eddy current measuring coil assemblies comprise a pair of bracelets, each containing a plurality of pancake coils.

7. The eddy current probe according to claim 4 wherein:
   each of the said coil assemblies is of the bobbin type.

8. The eddy current probe according to claim 4 wherein:
   each of the said coil assemblies comprises a bracelet containing a plurality of pancake coils.

9. The eddy current probe according to claim 3 wherein:
   the said magnetization means has a specific configuration to generate a predetermined magnetic field distribution.

10. The eddy current probe according to claim 4 wherein:
    the said magnetization means has a specific configuration to generate a predetermined magnetic field distribution.

11. The eddy current probe according to claim 4 wherein:
    said eddy current measuring means comprise three eddy current measuring coil assemblies located spaced apart axially from each other at locations of three different saturation levels.

12. An eddy current probe for detecting defects in a tube made of a ferro-magnetic material, comprising:
    a probe housing made of a non-ferromagnetic material and shaped to be introduced into the tube for inspection, said housing having an axis substantially coinciding with the axis of the tube under inspection when the probe is in use;
    magnetization means for generating a magnetic field within the probe housing and for magnetizing said tube to partial saturation levels, said magnetization means having a specific configuration to generate a predetermined magnetic field distribution, and
    at least two substantially identical eddy current measuring means in said housing, the said eddy current measuring means being spaced apart axially from each other at locations of different saturation levels.

13. The eddy current probe according to claim 12 wherein:
    one of the said at least two eddy current measuring means is positioned at the maximum partial saturation level; and
    each of the others thereof is positioned at a saturation level different from the said maximum level.

14. The eddy current probe according to claim 13 wherein:
    each of the said current measuring means comprises a pair of identical eddy current measuring coil assemblies, electrically connected to operate in the differential probe configuration.

15. The eddy current probe according to claim 13 wherein:
    the said at least two substantially identical eddy current measuring means comprise at least two substantially identical eddy current measuring coil assemblies located spaced apart axially from each other at locations of different saturation levels and a common reference coil, all electrically connected to operate in the absolute probe configuration.

16. The eddy current probe according to claim 14 wherein:
    the said pair of eddy current measuring coil assemblies are of bobbin type.

17. The eddy current probe according to claim 14 wherein:
    the said pair of eddy current measuring coil assemblies comprise a pair of bracelets, each containing a plurality of pancake coils.

18. The eddy current probe according to claim 15 wherein:
    each of the said coil assemblies is of the bobbin type.

19. The eddy current probe according to claim 15 wherein:
    each of the said coil assemblies comprises a bracelet containing a plurality of pancake coils.

* * * * *